(12) United States Patent
Farzin-Nia

(10) Patent No.: US 7,581,949 B2
(45) Date of Patent: Sep. 1, 2009

(54) DEBONDING PLIERS

(75) Inventor: Farrokh Farzin-Nia, Inglewood, CA (US)

(73) Assignee: Ormco Corporation, Orange, CA (US)

( * ) Notice: Subject to any disclaimer, the term of this patent is extended or adjusted under 35 U.S.C. 154(b) by 71 days.

(21) Appl. No.: 11/563,592

(22) Filed: Nov. 27, 2006

(65) Prior Publication Data
US 2007/0122763 A1    May 31, 2007

Related U.S. Application Data

(60) Provisional application No. 60/740,027, filed on Nov. 28, 2005.

(51) Int. Cl.
| | |
|---|---|
| A61C 9/00 | (2006.01) |
| A61C 3/14 | (2006.01) |
| B25C 11/00 | (2006.01) |
| B21F 1/00 | (2006.01) |
| B21F 15/02 | (2006.01) |
| B25B 7/00 | (2006.01) |

(52) U.S. Cl. .............. 433/4; 433/159; 254/22; 140/106; 140/121; 81/300

(58) Field of Classification Search ............ 433/4, 433/8, 40, 159, 160; D24/153; 140/106, 140/121; 81/302, 303, 308, 426; 254/22
See application file for complete search history.

(56) References Cited

U.S. PATENT DOCUMENTS

| | | |
|---|---|---|
| 331,954 A | 12/1885 | Fish et al. |
| 505,835 A | 10/1893 | Kulp et al. |
| 511,067 A | 12/1893 | Walter |

(Continued)

FOREIGN PATENT DOCUMENTS

| | | |
|---|---|---|
| EP | 0793948 A1 | 10/1997 |
| WO | 84-04238 A1 | 11/1984 |

OTHER PUBLICATIONS

Deva Devanathan, Design and Development Of An Advanced Ceramic Bracket, TP Orthodontics, Inc., 1997, 9 pages.

(Continued)

*Primary Examiner*—Ralph A Lewis
*Assistant Examiner*—Yogesh Patel
(74) *Attorney, Agent, or Firm*—Wood, Herron & Evans, LLP

(57) ABSTRACT

An instrument for debonding an orthodontic bracket from a tooth surface includes first and second plier portions coupled for relative pivotal movement. A lever arm pivotally movable relative to the first and second plier portions has a tooth engaging member on a first end. In one embodiment, the tooth engaging member is positioned on the lever arm for movement between a jaw of the plier portions and the tooth surface when a second end of the lever arm is pivotally manipulated in a direction toward a handle of the plier portions. In another embodiment, at least part of at least one plier portion is flexible relative to the lever arm such that the lever arm moves the tooth engaging member relative to a jaw of the plier portions after the bracket engaging portions are engaged with the orthodontic bracket and the handles and lever arm pivotally manipulated toward one another.

23 Claims, 14 Drawing Sheets

U.S. PATENT DOCUMENTS

| | | | |
|---|---|---|---|
| 979,609 A | 12/1910 | Vaughn | |
| 1,094,269 A | 4/1914 | Taylor | |
| 1,328,423 A * | 1/1920 | Davies | 140/121 |
| 1,633,533 A | 6/1927 | Kern | |
| 1,793,679 A | 2/1931 | Chilofsky | |
| 2,214,985 A | 9/1940 | Bachmann | |
| 2,347,300 A | 4/1944 | Thierwechter | |
| 2,497,254 A | 2/1950 | Brantley | |
| 2,578,985 A * | 12/1951 | Schmidt | 140/109 |
| 2,853,074 A * | 9/1958 | Olson | 227/177.1 |
| 3,046,659 A * | 7/1962 | Tofflemire | 433/39 |
| 3,244,201 A | 4/1966 | Wallshein | |
| 3,360,018 A | 12/1967 | Lindsay | |
| 3,507,043 A * | 4/1970 | Rubin | 433/4 |
| 3,675,359 A | 7/1972 | Ohno | |
| 3,755,902 A | 9/1973 | Northcutt | |
| 3,825,990 A * | 7/1974 | Shields | 29/268 |
| 3,986,265 A | 10/1976 | Cusato | |
| 4,018,110 A * | 4/1977 | Spriggs | 81/3.08 |
| 4,197,647 A | 4/1980 | Goldenthal | |
| 4,310,305 A | 1/1982 | Frajdenrajch | |
| 4,435,160 A | 3/1984 | Randklev | |
| 4,514,171 A | 4/1985 | Kurz | |
| 4,553,932 A | 11/1985 | Armstrong et al. | |
| 4,600,381 A | 7/1986 | Hodgson | |
| 4,631,028 A | 12/1986 | Kurz | |
| 4,776,791 A | 10/1988 | Hannula et al. | |
| 4,820,545 A | 4/1989 | Negrych | |
| 4,902,224 A | 2/1990 | Collins et al. | |
| 4,904,183 A | 2/1990 | Hannan et al. | |
| 4,915,625 A | 4/1990 | Tsukuma et al. | |
| 4,950,157 A | 8/1990 | Cleary | |
| 5,011,403 A | 4/1991 | Sadoun et al. | |
| 5,062,793 A | 11/1991 | Cleary et al. | |
| 5,064,369 A | 11/1991 | Kawaguchi | |
| 5,066,225 A | 11/1991 | Forbes Jones et al. | |
| 5,071,344 A | 12/1991 | Wong et al. | |
| 5,092,074 A * | 3/1992 | Zincke | 43/53.5 |
| 5,098,288 A | 3/1992 | Kesling | |
| 5,158,452 A | 10/1992 | Franseen et al. | |
| 5,161,969 A | 11/1992 | Pospisil et al. | |
| 5,197,873 A | 3/1993 | Wong et al. | |
| 5,261,814 A | 11/1993 | Farzin-Nia et al. | |
| 5,269,680 A | 12/1993 | Kawaguchi | |
| 5,288,230 A | 2/1994 | Nikutowski et al. | |
| 5,362,232 A | 11/1994 | Franseen et al. | |
| 5,366,372 A | 11/1994 | Hansen et al. | |
| 5,380,196 A | 1/1995 | Kelly et al. | |
| 5,439,379 A | 8/1995 | Hansen | |
| 5,480,301 A | 1/1996 | Farzin-Nia et al. | |
| 5,545,168 A * | 8/1996 | Burke | 606/74 |
| 5,645,421 A | 7/1997 | Slootsky | |
| 5,746,594 A | 5/1998 | Jordan et al. | |
| 6,382,965 B1 * | 5/2002 | Ruiz-Vela et al. | 433/4 |
| 6,446,854 B1 | 9/2002 | Remiszewski et al. | |
| 2003/0152883 A1 | 8/2003 | Smith et al. | |

OTHER PUBLICATIONS

ORMCO Corporation, It's Time To Take A Closer Look At Aesthetics . . . , 1999, 4 pages.

Samir E. Bishara et al., Comparisons Of Different Debonding Techniques For Ceramic Brackets: An in Vitro Study, Part I, Background and Methods, American Journal of Orthodontics, Aug. 1990, 12 pages.

Samir E. Bishara et al., Comparisons Of Different Debonding Techniques For Ceramic Brackets: An in Vitro Study, Part II, Findings and Clinical Implications, American Journal of Orthodontics, Sep. 1990, 13 pages.

Samir E. Bishara et al., Comparisons Of Effectiveness Of Pliers With Narrow And Wide Blades In Debonding Ceramic Brackets, American Journal Orthodontics, Mar. 1990, 4 pages.

Michael L. Swartz, Ceramic Brackets, Journal of Clinical Orthodontics, Feb. 1988, 7 pages.

Samir E. Bishara et al., Evaluation Of Debonding Characteristics Of A New Collapsible Ceramic Bracket, American Journal Orthodontics, Nov. 1997, 4 pages.

ORMCO Corporation, Orthodontic Product Catalog, 1999, 6 pages.

UNITEK Corporation, Effects Of Debonding Transcend Ceramic Orthodontic Brackets From Human Enamel: An In Vitro Examination, 1988, 4 pages.

ORMCO Corporation, inspire! Bracket Identification And Placement, Undated, 3 pages.

ORMCO Corporation, For Aesthetics, There Is Only One Clearly Superior Choice . . . , Undated, 4 pages.

European Patent Office Search Report in European Application No. 06256075.0 dated Apr. 27, 2007.

* cited by examiner

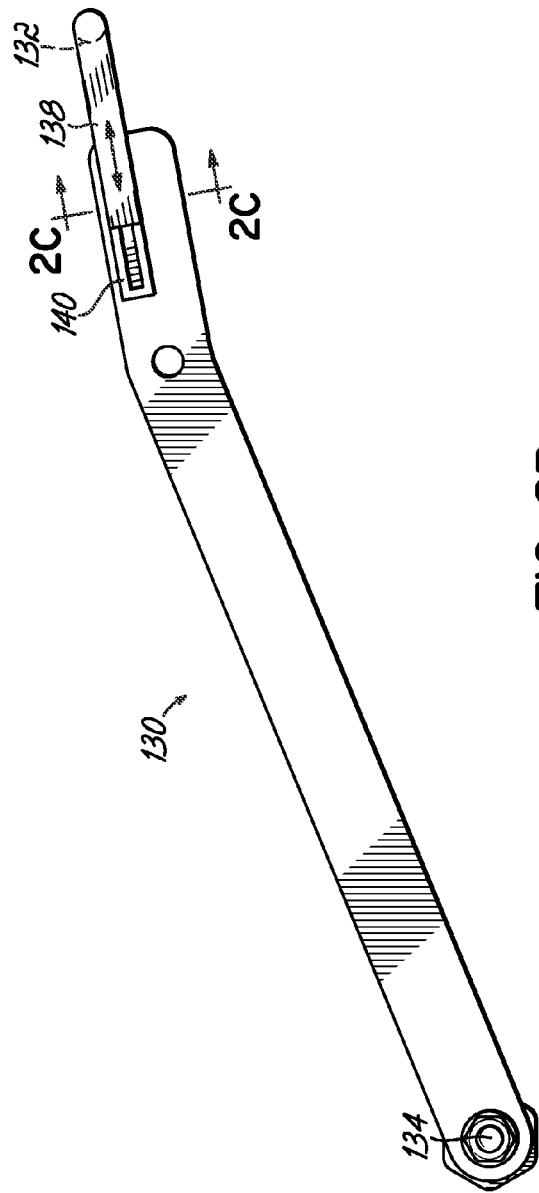
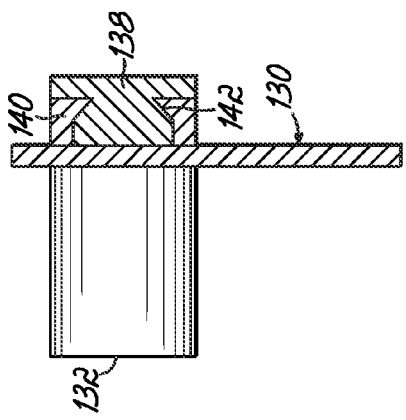
FIG. 2B
FIG. 2C

DEBONDING PLIERS

CROSS REFERENCE TO RELATED APPLICATION

This application claims priority to U.S. Provisional Patent Application Ser. No. 60/740,027, filed Nov. 28, 2005, and incorporated by reference herein in its entirety.

TECHNICAL FIELD

The present invention relates generally to a debonding tool and technique used for removing orthodontic brackets from the teeth of a patient.

BACKGROUND

One of the major challenges associated with the use of brackets for orthodontic treatment is the removal of the brackets from the teeth of the patient. Metal brackets are generally removed by pinching the bracket in a generally mesio-distal or diagonal direction using a pair of pliers, such as so-called Weingart pliers. The pliers apply compressive forces and pinch the brackets generally in a mesio-distal direction, typically by placing the jaws of the pliers diagonally across the bracket and engaging the tie-wings at opposite corners of the bracket, for example, at the gingival/mesio and occlusal/distal corners of the bracket. Pinching the bracket in this manner results in deformation of the ductile bracket body as well as the debonding pad used to attach the body of the bracket to the tooth surface. This deformation causes the interface between the adhesive and the bonding pad or bracket base to separate or fracture, thereby essentially peeling the bracket away from the tooth surface as the adhesive material debonds.

Brittle orthodontic bracket materials, such as ceramic materials, are much more problematic during the bracket debonding process. These bracket materials are extremely hard and non-ductile relative to materials, such as stainless steel, typically used for metal brackets. Ceramic materials also have a low fracture toughness relative to steel and other metals, meaning that ceramic material is much more prone to fracture, rather than deformation, under an applied force. An attempt to pinch the tie wings of a ceramic bracket in the manner described above for metal brackets generally results in fracture of the tie wings or other portions of the bracket due to point loading of the bracket material by the pliers at the contact points.

For these and other reasons, such as heightened sensitivity to surface imperfections, various tools and methods have been proposed and used for debonding a bracket from a tooth. However, many tools and/or methods have not been fully satisfactory. For example, plier-type tools having metal jaws with sharp, opposed edges have been directed into the adhesive interface between the bracket base and the tooth. These tools separate the bracket base from the tooth surface by applying force directly to the adhesive interface.

U.S. Pat. No. 4,904,183, issued to Hannan, discloses a torquing tool having slotted ends which closely fit over the mesial and distal bracket surfaces. The user applies a twisting force about an axis generally normal to the bracket base and tooth surface to fracture the adhesive bond therebetween. This reference discloses that the tool is especially useful with brackets made of brittle, ceramic material.

U.S. Pat. No. 5,062,793, issued to Cleary, discloses a debonding instrument having a pair of arms with pulling sections adapted to engage a bracket behind its occlusal and gingival tie wings. The arms are connected to a lever, and movement of the lever enables the arms to simultaneously exert a pulling force on both of the wings along substantially their entire mesial-distal width in order to lift the bracket from the tooth in a straight-line fashion.

However, a torsional force, such as the quick twisting force or motion disclosed by Hannan, to be applied to the patient's tooth can be very uncomfortable for the patient. Further, depending on the bracket material and bond strength, these methods often require an excessive amount of force making it difficult to separate the bracket from the tooth. Such excessive force or methods may result in damage to the tooth surface or increased discomfort. Accordingly, dentists are hesitant to use such force, particularly in a torsional or pivoting action, to debond brackets.

U.S. Pat. Nos. 5,366,372 and 5,439,379, both issued to Hansen, disclose an orthodontic bracket having mesial and distal sections debonded from the tooth by pivoting the sections toward each other in respective arcs about a central reference axis extending in an occlusal-gingival direction. The mesial and distal sections are discrete and spaced apart from each other, or alternatively, integrally joined by a relatively thin web that bends and optionally fractures upon debonding. However, such design, when debonded by dentists may result in breakage or fracture of the bracket, even with less force than traditionally required, resulting in discomfort, and presenting potential harm from the pieces of the broken bracket in the patient's mouth.

An improved debonding technique has been described in U.S. Pat. No. 6,382,965 and discusses the use of a pivoting or rocking motion to break the bond between the adhesive and the bracket base. While this method has been quite successful, it would still be desirable to further decrease discomfort to the patient during debonding. In particular, it would be desirable to further reduce the amount of force needed to remove the bracket from the patient's tooth while retaining the necessary bonding forces during the orthodontic treatment. Another goal is to decrease the chances of having a nonmetal bracket break during debonding.

SUMMARY

In one embodiment, an instrument for debonding an orthodontic bracket from a surface of a tooth includes first and second plier portions coupled for pivotal movement relative to one another. Each plier portion has a respective handle and a jaw for engaging the bracket. The instrument further includes a lever arm that is pivotally movable relative to the first and/or second plier portions and that has a tooth engaging member on a first end. The tooth engaging member is positioned on the lever arm such that it is moved between a jaw and the tooth surface when the jaws are engaged with the orthodontic bracket and a second end of the lever arm is pivotally manipulated in a direction toward a handle of the plier portions.

In another embodiment, an instrument for debonding an orthodontic bracket from a surface of a tooth includes first and second plier portions coupled for pivotal movement relative to one another. Each plier portion has a respective handle and a jaw for engaging the bracket. The instrument further includes a lever arm that is pivotally movable relative to the first and/or second plier portions and that has a tooth engaging member on a first end. At least part of at least one of the plier portions is more flexible than the lever arm such that the lever arm moves the tooth engaging member relative to a jaw after the jaws are engaged with the orthodontic bracket and the handles and lever arm pivotally manipulated in directions toward one another.

In yet another embodiment, an instrument for debonding an orthodontic bracket from a surface of a tooth includes first and second plier portions, as described above, and a lever arm pivotally movable relative to at least one of the plier portions. The lever arm has a tooth engaging member that is selectively adjustable to vary a position of the tooth engaging member relative to a jaw of the plier portions.

In yet another embodiment, a tool is used to debond an orthodontic bracket that has been attached to a tooth with adhesive. The tool includes pliers having at least one tip for engaging the bracket, and a tooth engaging member attached to the pliers and is movable adjacent the exterior of the tip. A method of debonding the orthodontic bracket using the tool includes engaging at least a first side of the bracket with the at least one tip. The tooth engaging member is positioned between the tooth and the at least one tip. The bracket is pivoted about an axis lying in a plane generally parallel to a plane defined by the base and the tooth engaging member is pressed against the tooth to thereby apply a tensile force to a first side of the bracket in a direction away from the tooth, the tensile force applied to the first side being substantially greater than any tensile force directed away from the tooth which may be applied to the side of the bracket located opposite to the first side. The adhesive is thereby fractured between the bracket and the tooth to remove the bracket from the tooth.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIGS. 2B and 2C depict in side elevation view and cross-sectional view, respectively, an alternative embodiment of an attachment for the debonding tool in accordance with the present invention.

DETAILED DESCRIPTION

In accordance with the present invention, a debonding tool for removing an orthodontic bracket from a tooth is provided, the tool being a plier-type tool having two tip portions for engaging the bracket and an attachment that includes a tooth engaging member that engages the tooth adjacent one of the tip portions to help peel the bracket from the tooth. The debonding tool of the present invention and the method of debonding a bracket using the tool will now be described with reference to the Figures, wherein like numerals are used to refer to like parts.

Figure 1:
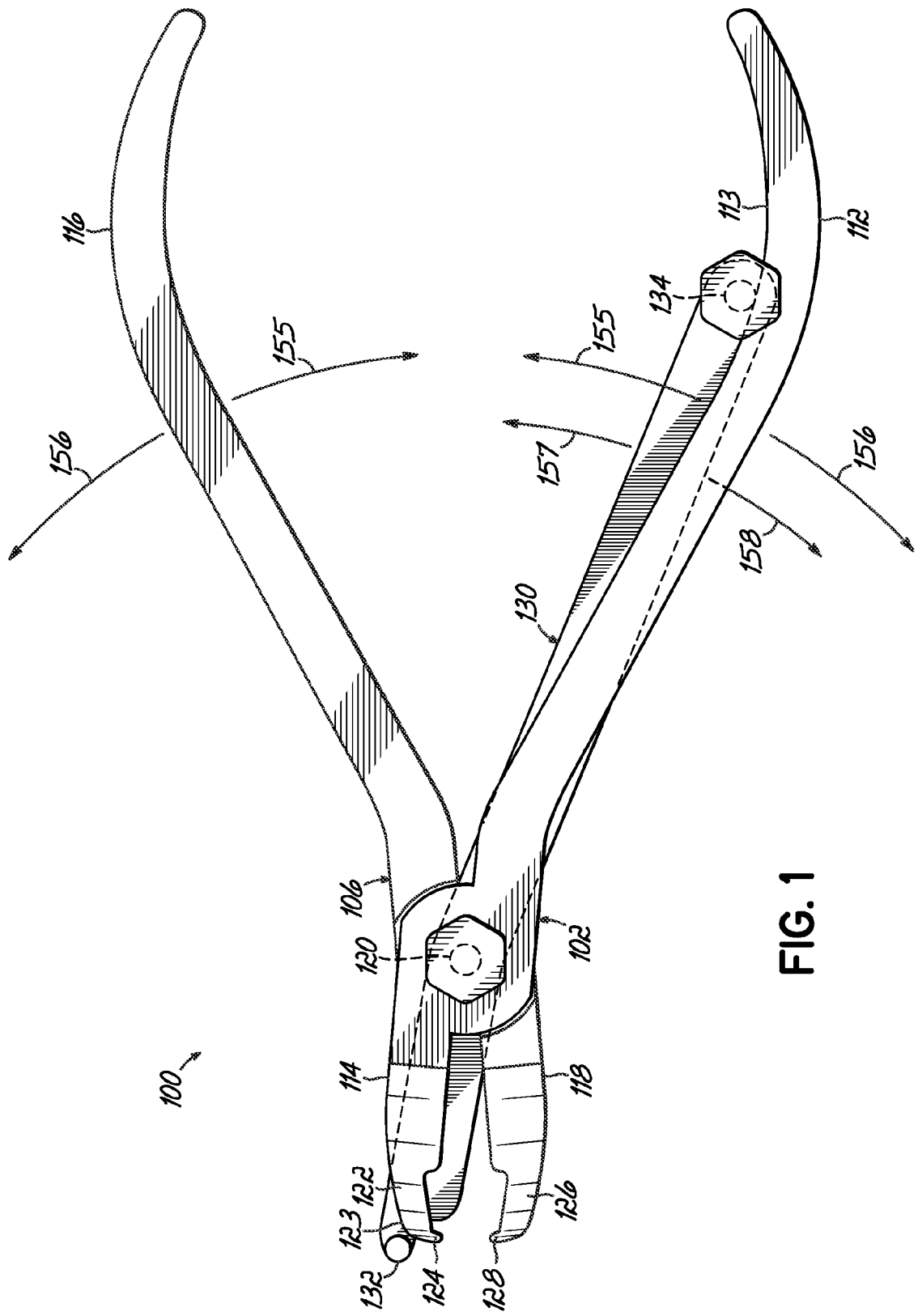
FIG. 1 illustrates a first side elevation view of one exemplary embodiment of a debonding tool for removing an orthodontic bracket in accordance with the present invention.
Figure 2:
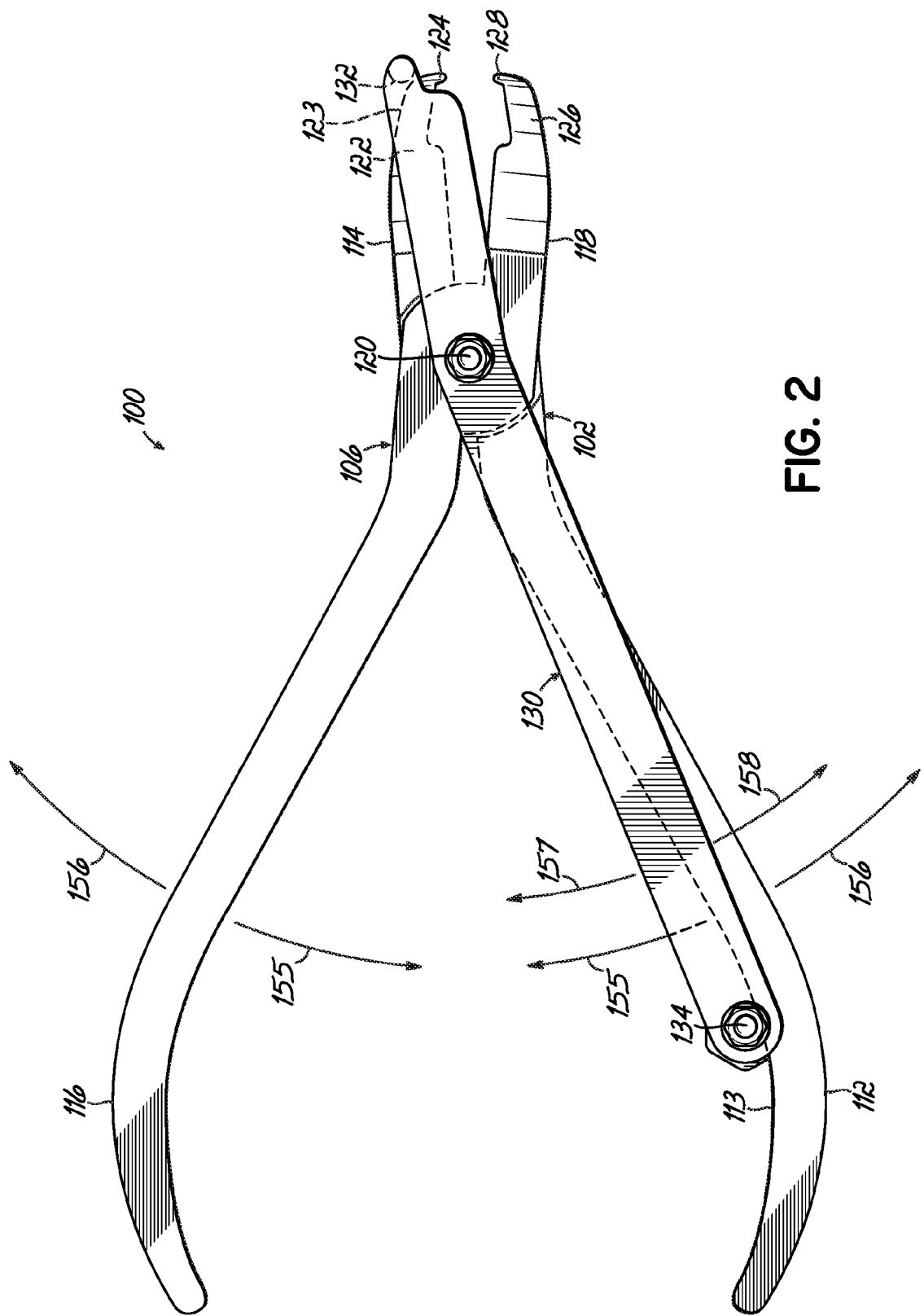
FIG. 2 illustrates a second and opposing side elevation view of the debonding tool of FIG. 1.

FIGS. 1 and 2 illustrate opposing side views of one embodiment of a tool 100 taking the general form of a pair of pliers having a first plier portion 102 and a second plier portion 106. First plier portion 102 includes a first handle 112 and a first jaw 114, which may be formed integrally together. Second plier portion 106 includes a second handle 116 and a second jaw 118, which may also be formed integrally together. Handle and jaw 112, 114 of first plier portion 102 are pivotally coupled to handle and jaw 116, 118 of second plier portion 106 by a pivot pin 120. It will be appreciated that the first and second plier portions may alternatively be formed with complementary features to provide pivotal coupling without the need for a pin 120. First jaw 114 includes a first bracket engaging portion 122 having a first nib 124, and second jaw 118 includes a second bracket engaging portion 126 having a second nib 128. Nibs 124, 128 project toward one another, and are configured to grip an orthodontic bracket under the tie wings when first and second bracket engaging portions 122, 126 are in an engaged position, as will be described further below. While first and second bracket engaging portions 122, 126 are shown and described herein as including respective nibs 124, 128, it will be understood that the first and second bracket engaging portions may alternatively comprise other structure adapted to engage an orthodontic bracket. Handles 112, 116 may be moved towards one another, as illustrated by arrows 155, to engage or grip a bracket, and moved away from each other, as illustrated by arrows 156 to disengage the bracket.

In the embodiment shown, tool 100 further includes a lever arm 130 attached to the first and second plier portions 102, 106 by the pivot pin 120. The lever arm 130 includes a tooth engaging member, depicted herein as a pin 132, adjacent an exterior surface 123 of the first engaging portion 122, i.e., positioned away from the opposing second engaging portion 126. Tool 100 may be configured to facilitate movement of lever arm 130 with the first handle 112 of the first plier portion 102. In the embodiment shown, lever arm 130 further includes an opposing pin 134 adjacent an interior surface 113 of the first handle 112, i.e., positioned toward the opposing second handle 116, to facilitate movement of lever arm 130 with first handle 112. It will be appreciated, however, that lever arm 130 may alternatively include a protrusion instead of pin 132, or may otherwise be configured so that lever arm 130 can be moved with first handle 112. In an exemplary embodiment, the lever arm 130 is free to swivel around the pivot pin 120 independently of the first and second plier portions 102 and 106, as indicated by arrows 157 and 158.

Figure 2A:
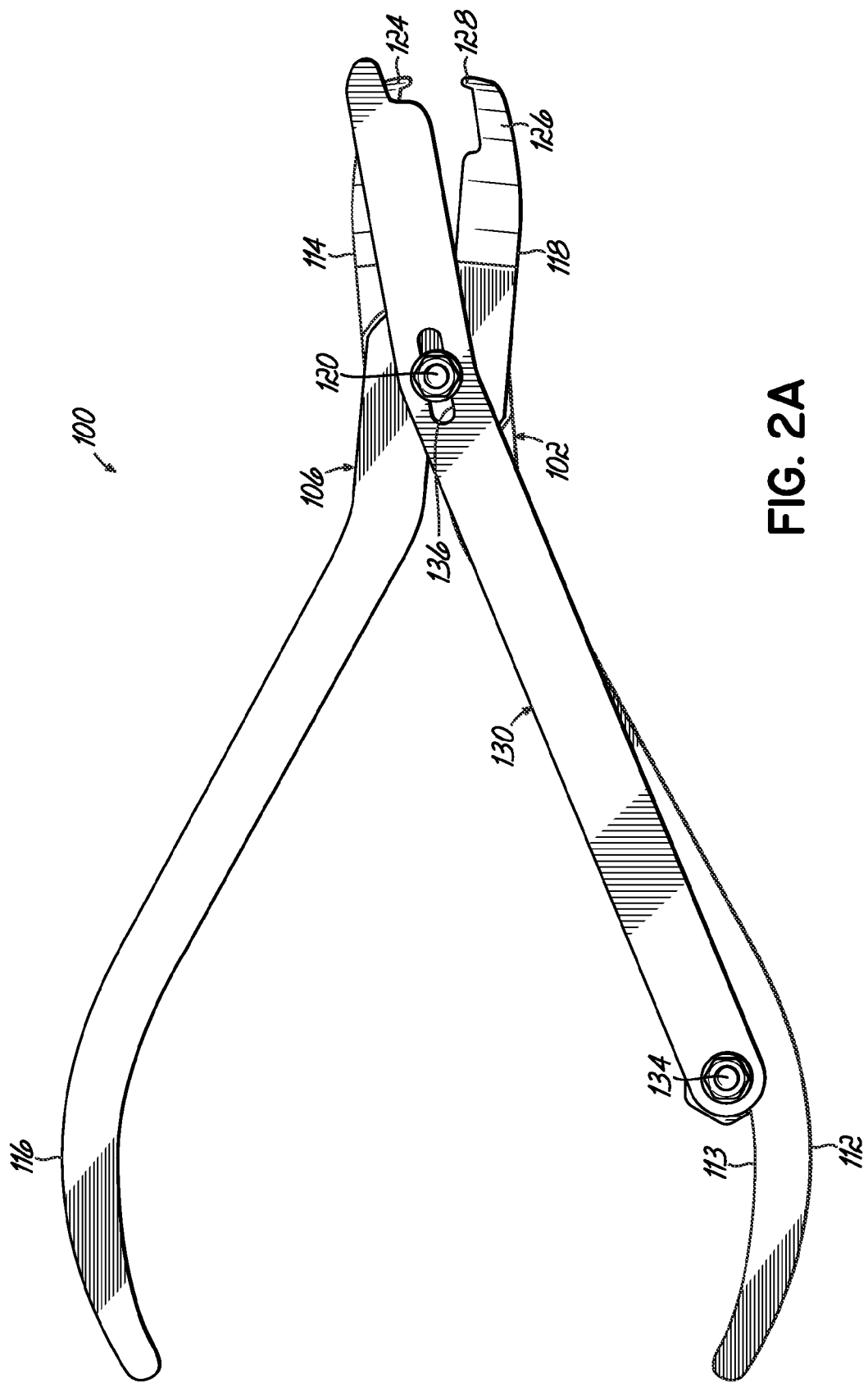
FIG. 2A illustrates a side elevation view of another exemplary embodiment of a debonding tool for removing an orthodontic bracket in accordance with the present invention.

As illustrated in a side elevation view in FIG. 2A, the lever arm 130 may include an elongate slot 136 through which the pivot pin 120 is inserted such that the joint between the plier portions 102, 106 and the lever arm 130 is adjustable, thereby enabling the orthodontic practitioner to adjust the position of the tooth engaging pin 132 making the lever arm 130 self-adjusting, such that the pin 132 can ride on the exterior surface 123. The lever arm 130 can freely and independently move the pin 132 relative to the exterior surface 123 of first bracket engaging portion 122.

As illustrated in a side elevation view in FIG. 2B, in another embodiment, the portion of the lever arm 130 between the pivot pin 120 and the pin 132 may be extendable (adjustable) by connecting the pin 132 to a sliding insert 138 that can slidably move inside a housing 140 in the lever arm 130. By way of example and not limitation, a dovetail joint 142 may be used to hold the sliding insert 138 in the housing 140. Pin 132 can thus rest on the exterior surface 123 and can slide along the surface 123 as the pin 132 is forced into engagement with a tooth, as described below.

Figure 3:
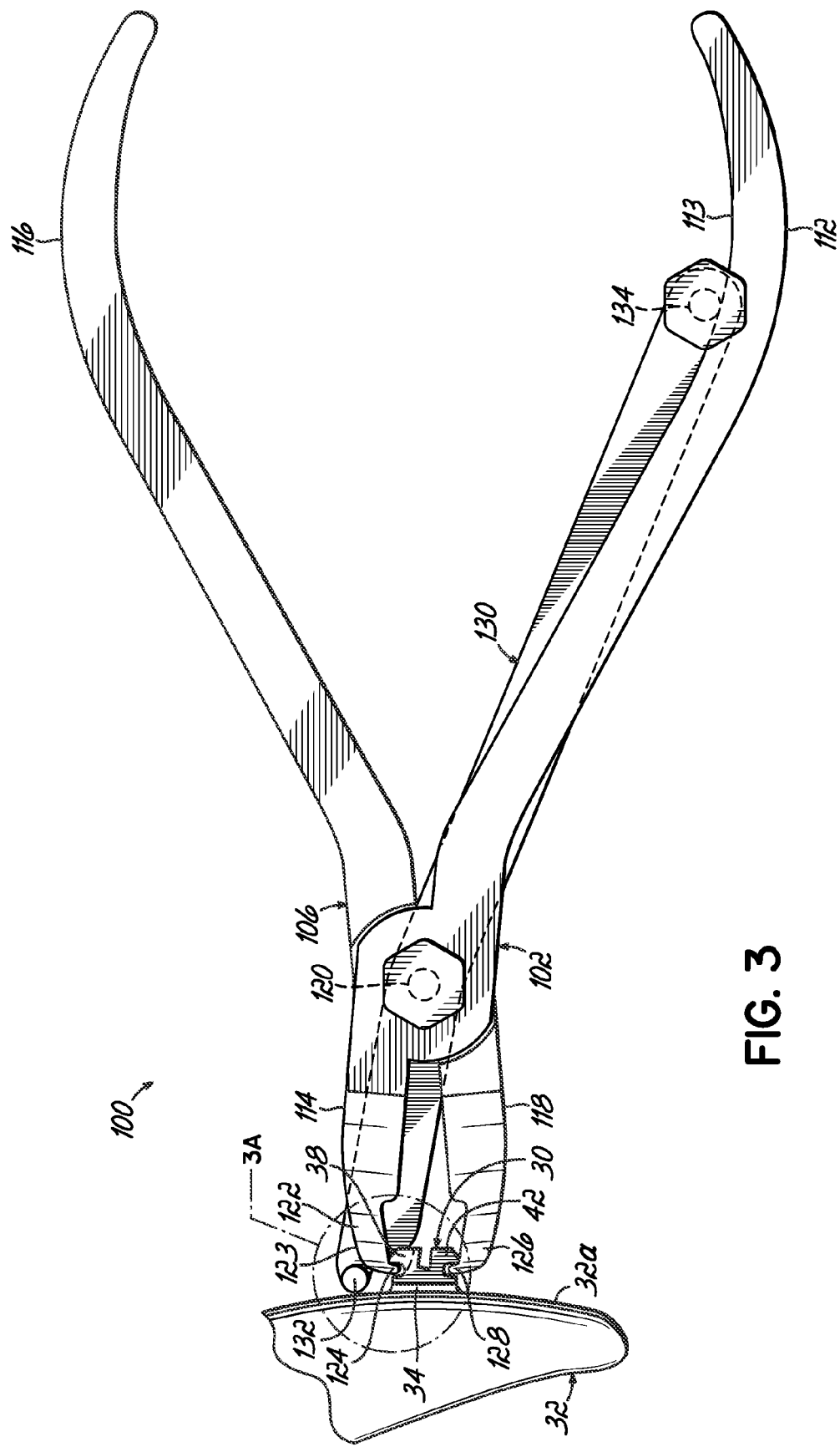
FIG. 3 is a side elevation view showing the debonding tool of FIG. 1 initially gripping an orthodontic bracket that is adhesively bonded to a tooth.
Figure 3A:
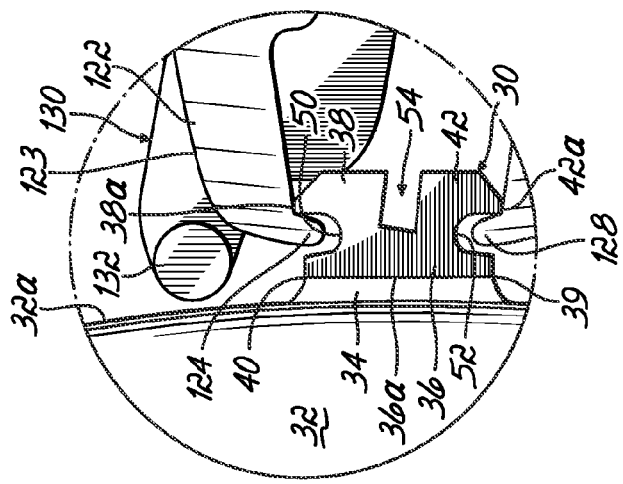
FIG. 3A is a fragmented, enlarged view from FIG. 3 of the nib of the debonding tool engaging the bracket.

FIGS. 3 and 3A depict in side elevation view and in an enlarged view, respectively, the tool 100 positioned to engage a bracket 30 bonded on a tooth 32. Bracket 30, as shown, includes a base 36 having a bonding surface 36a on which an adhesive layer 34 is applied to bond the bracket 30 to the tooth surface 32a. The base 36 of the bracket 30 has an occlusal edge 39 and an opposing gingival edge 40. Bracket 30 further includes a gingival tie wing 38 separated from an occlusal tie wing 42 by an archwire slot 54 extending mesially-distally, and recesses 50, 52 under the respective tie wings 38, 42 separating them from the base 36. The first and second bracket engaging portions 122, 126 are positioned to engage the bracket 30 on the gingival and occlusal sides, respectively. Nib 124 extends into recess 50 to engage the bracket 30 under the gingival tie wing 38, and nib 128 extends into recess 52 to engage the bracket 30 under the occlusal tie wing 42. Tooth engaging pin 132 of lever arm 130 is positioned adjacent the tooth surface 32a and adjacent the exterior surface 123 of first bracket engaging portion 122 on the side of bracket 30 proximate the gingival edge 40. In an exemplary embodiment, the lever arm is shaped such that it will not interfere with an archwire positioned in archwire slot 54 in the event debonding of the brackets 30 is desirable with the archwire still engaged in the slots 54.

Figure 4A:
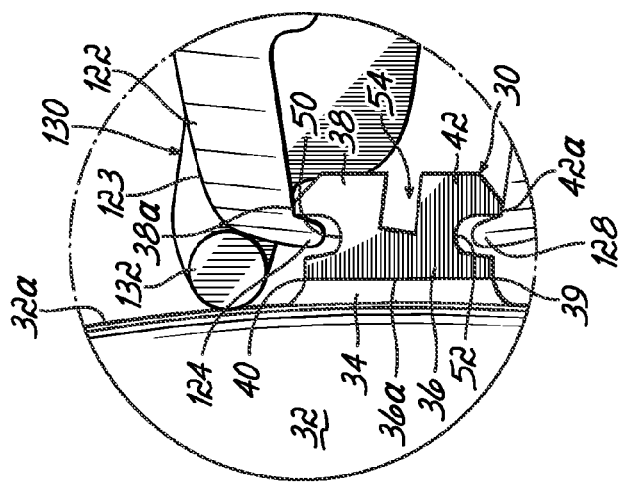
FIGS. 4A and 4B are fragmented, enlarged views of the tooth engaging pin between the bracket engaging portion of the debonding tool and the tooth.
Figure 4:
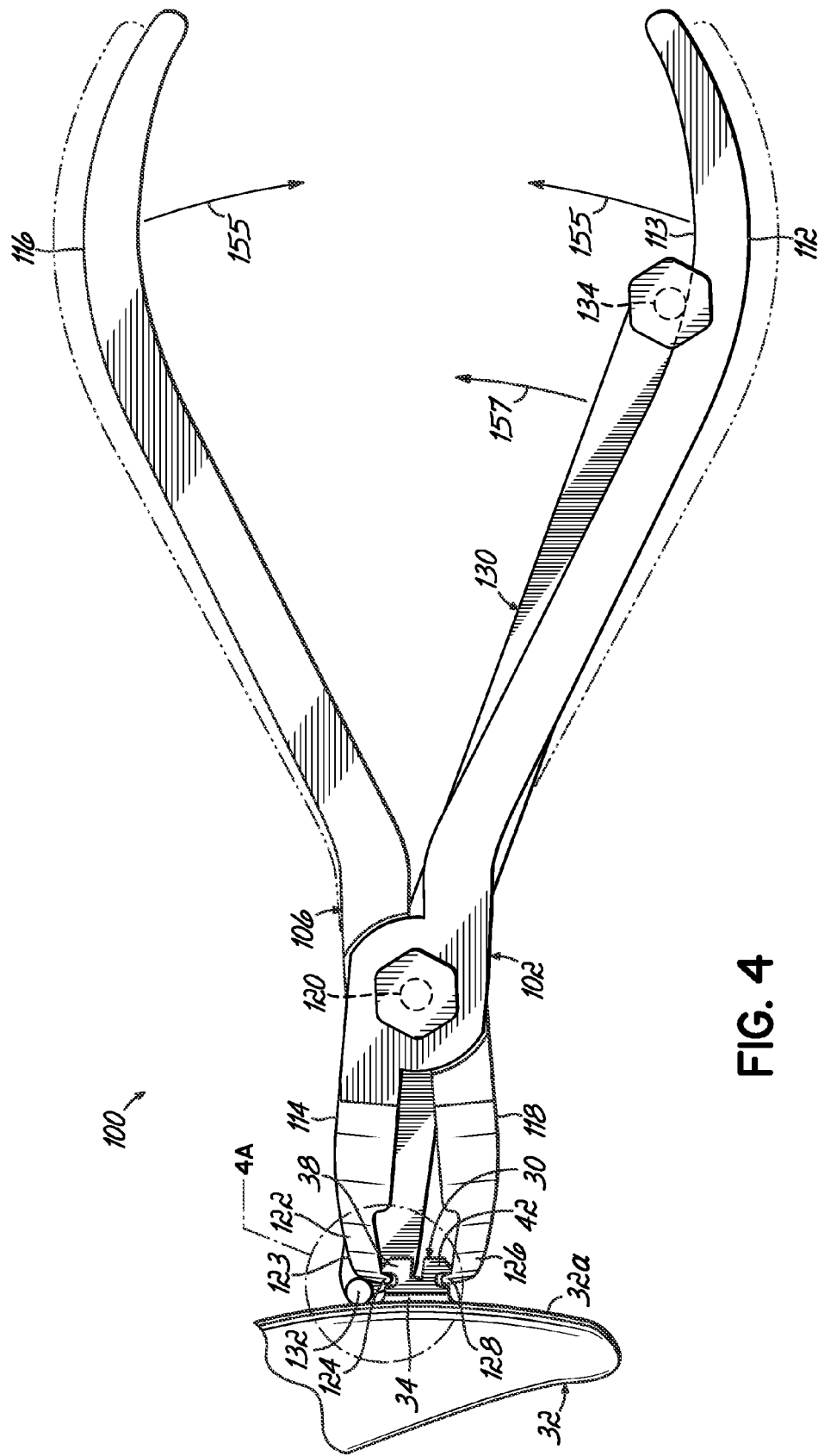
FIG. 4 is a side elevation view similar to FIG. 3, but showing the handles of the debonding tool forced toward each other to rotate the tooth engagement pin into contact with the tooth in accordance with the invention.
Figure 4B:
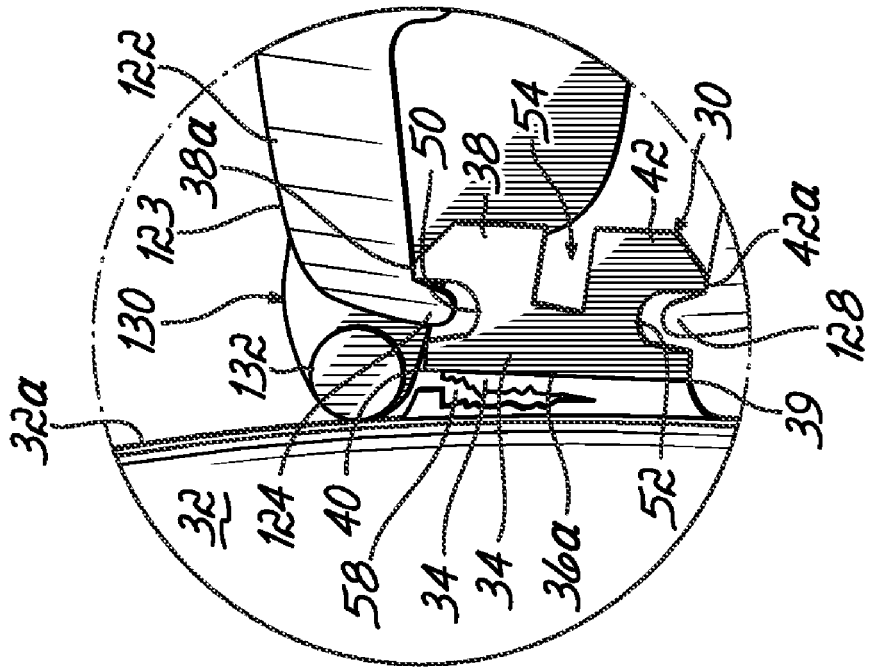

FIGS. 4 and 4A-4B are similar to FIGS. 3 and 3A, respectively, but further show the tool 100 in operation as an orthodontic practitioner urges or squeezes the first and second handles 112 and 116 towards each other in the direction of arrows 155. As the handles 112, 116 move inward, the first and second bracket engaging portions 122, 126 further engage the tie wings 38 and 42, and the first handle 112 urges the opposing pin 134 inward in the direction of arrow 157 likewise causing the tooth engaging pin 132 inward toward the bracket 30 and into engagement with tooth surface 32a. The tooth engaging pin 132 pushes against the tooth 32 to cause a peeling action at the gingival edge 40 of bracket base 36. The force provided by the tooth engaging pin 132 is a rotational torque about an axis that is in the same plane as the tooth enamel surface, which results in the peeling force that urges the bracket 30 to lift away from the tooth surface 32a. In one embodiment, as shown in FIG. 4A, the tooth engaging pin 132 wedges between the tooth surface 32a and the exterior surface 123 of bracket engaging portion 122. In an alternative embodiment, as shown in FIG. 4B, the tooth engaging pin 132 engages the tooth surface 32a but does not contact the exterior surface 123 as the bracket is debonded. Thus, it is not essential that the pin 132 act as a wedge, but rather, only that it pushes against the tooth surface 32a to provide the rotational torque.

Figure 5A:
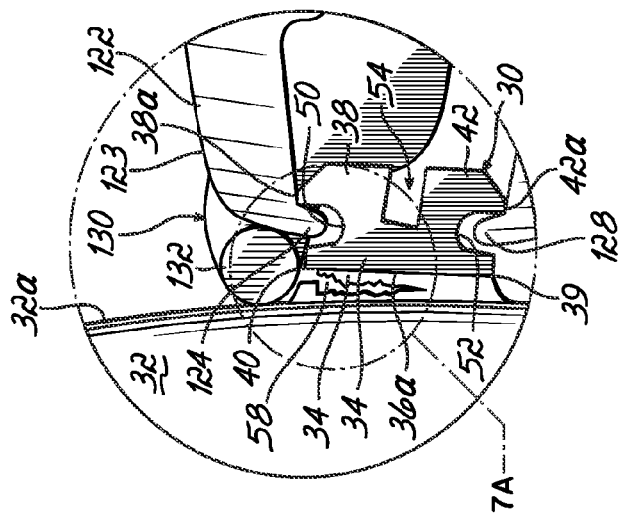
FIGS. 5A and 5B are fragmented, enlarged views of the breakage of the adhesive bond along the gingival side of the bracket during removal of the bracket from the tooth.
Figure 5B:
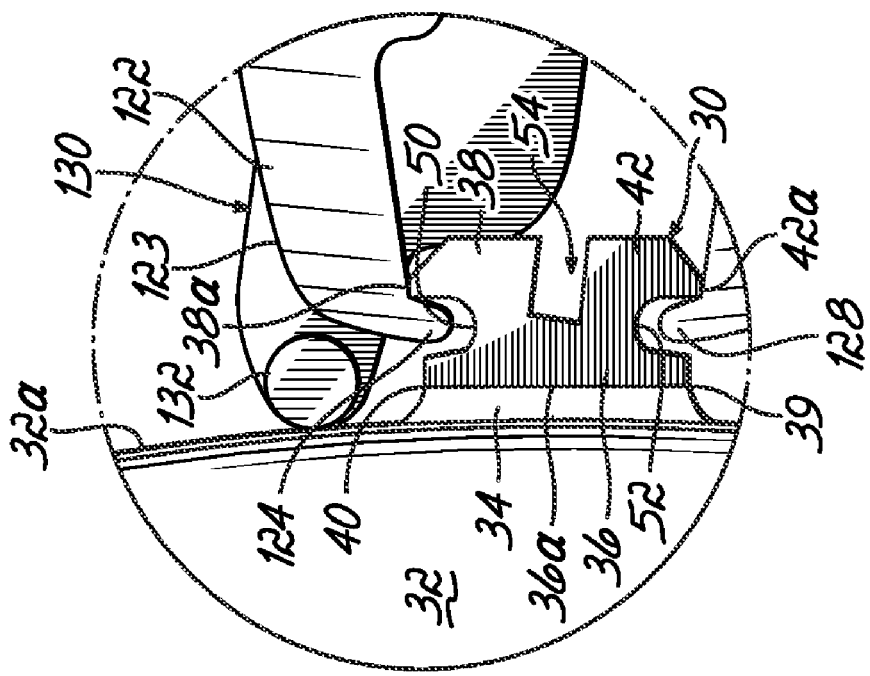
Figure 5:
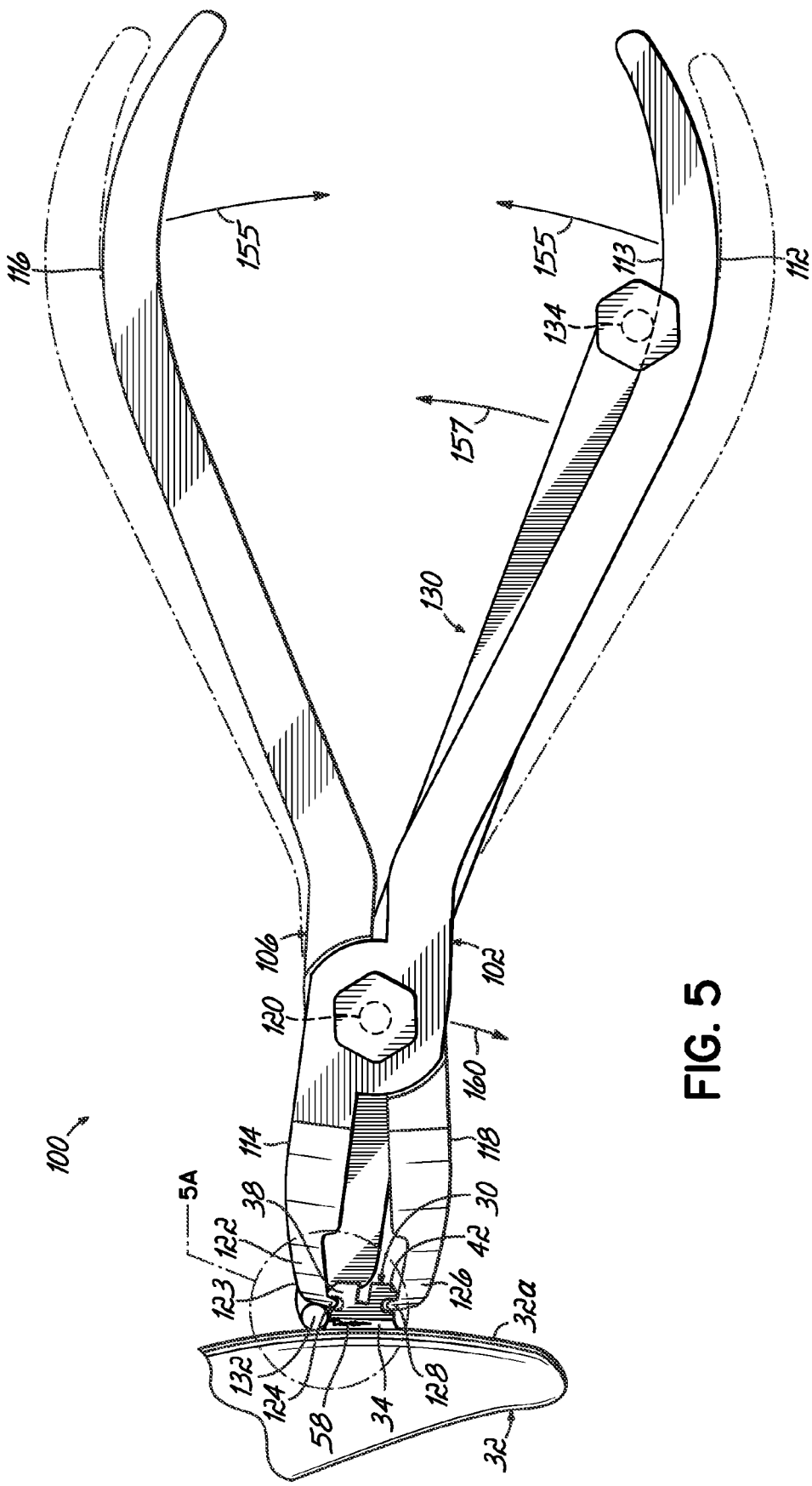
FIG. 5 is a side elevation view similar to FIG. 4, but showing the handles further squeezed and the tool rotated to break the adhesive bond between the bracket and the tooth.

FIGS. 5 and 5A-5B are similar to FIGS. 4 and 4A-4B, respectively, but further show the tool 100 in operation as the bracket is finally debonded. FIG. 5 illustrates rotation of tool 100 in a direction indicated by arrow 160 while grip pressure or compression is maintained on bracket 30 by engaging portions 122, 126 and opposed nibs 124, 128. A compressive grip is maintained on bracket 30 with nibs 124, 128 to permit a pivoting motion to be applied to bracket 30 and apply the required tensile force without having engaging portions 122, 126 and opposed nibs 124, 128 slip off bracket 30 while attempting to pivot bracket 30. The tooth engaging pin 132 continues inward toward the bracket 30 and continues to push against the tooth 32 to contribute further to the tensile force applied at the gingival edge 40 of bracket base 36. The rotational torque provided by the tooth engaging pin 132 and the rotation in the direction of arrow 160 take place about an axis line in a plane generally parallel to the plane of the base surface 36a, i.e., generally in the plane of tooth surface 32a as shown in FIG. 5A. In this manner, a tensile force is applied along the gingival edge 40 of bracket 30 in a direction away from tooth surface 32a. At the same time, compressive forces are applied to bracket 30 along the opposite occlusal edge 39 in a direction toward tooth surface 32a. In other words, unequal forces are applied in the tensile direction, i.e., a direction toward or away from tooth surface 32a, and a greater tensile force applied in a direction away from tooth surface 32a causes adhesive layer 34 to fracture or debond beginning adjacent the gingival edge 40 of bracket base 36.

Once a fracture 58 or debonding begins in this manner, the fracture 58 essentially propagates along this adhesive interface to the opposite end of the bracket 30, and bracket 30 debonds from tooth surface 32a. FIGS. 5 and 5A-5B further illustrate a portion of adhesive layer 34 remaining on tooth surface 32a, and another portion remaining on bracket base 36. Depending on the application, more or less of the adhesive layer 34 may be stripped from tooth surface 32a during this debonding process. The term "fracture" is used herein in a manner referring to each of these potential situations, i.e., some adhesive or no adhesive remaining on the tooth.

In accordance with an exemplary embodiment of the present invention, the first and second nibs 124, 128 engage a substantial portion of the tie wings 38, 42, respectively. Where the tie wings include a pair of gingival tie wings 38 and a pair of occlusal tie wings 42, the nibs 124, 128 may be sized so as to engage both wings in the respective pairs. Bracket engaging portions 122, 126 also make full contact with tie wings 38 and 42 along edges 38a and 42a. This full contact allows better gripping and avoids point loading of bracket 30, which could result in breaking or fracturing the bracket as compression is applied by jaws 114, 118. By contacting as much surface area as possible, the debonding forces are applied evenly to all the tie wings.

While the embodiments shown and described thus far include both nibs 124 and 128 engaging the bracket 30 under the respective tie wings 38, 42, it may be appreciated that debonding may still be achieved if only the nib 124, which is adjacent the tooth engaging pin 132, engages the bracket under gingival tie wing 38. The nib 128 could then be eliminated, such that jaw 118 includes only a bracket engaging portion 126 or an end portion that does not engage the bracket at all. For example, the end portion could merely rest on the tooth. Further, it may be appreciated that the bracket engaging portions 122, 126 may be differently designed without nibs so as to securely engage the bracket 30 while allowing the tooth engaging pin 132 to provide all or a majority of the force necessary to peel the bracket 30 off the tooth 32. In embodiments that do not utilize nibs that engage the bracket under the tie wings, it may then be possible to engage the bracket on the mesial and distial sides rather than the gingival and occlusal sides, or even diagonally, so as to firmly grip the bracket while the tooth engaging pin 132 provides all or a majority of the force necessary to peel the bracket 30 off the tooth 32.

One skilled in the art may also appreciate that the tool 100 can be flipped in the embodiments shown in FIGS. 3-5 such that the tooth engaging pin 132 is adjacent the occlusal edge 39 so as to peel the bracket 30 off tooth surface 36a in the occlusal-to-gingival direction. The tooth engaging pin 132 will then push against the tooth and apply a tensile force along the occlusal edge 39 of bracket 30 and a compressive force along the opposite gingival edge 40. Thus, tool 100 can be used to debond bracket 40 in any preferred direction.

Brackets 30 may be formed of suitable materials, including, without limitation, metals, ceramic, plastic and other suitable materials. Particularly, crystalline materials, such as crystalline forms of aluminum oxide or other metal salts, are suitable materials for bracket 30. Single crystalline aluminum oxide (sapphire) brackets may be machined from a single, grown crystal and heat polished to eliminate surface flaws such as cracks and chips occurring during machining. Such an aluminum oxide crystalline bracket generally does not adhere or stick to conventional adhesives used by orthodontists and, therefore, provides advantages in accordance with the present invention.

In an exemplary embodiment to further avoid breaking or fracturing bracket 30, and especially breaking one or more of the tie wings 38 and 42, at least bracket engaging portions 122, 126, including nibs 124, 128 may be formed from a relatively soft material as compared to bracket 30, i.e., a material that is less hard than the bracket material. "Hardness" refers to a measure of resistance of a material to surface indentation or abrasion, or the ability of a material to resist plastic deformation. The ability to resist plastic deformation is dependent on the modulus of elasticity (Young's modulus) of the material, which is a measure of the stiffness or rigidity of a material. Thus, a material with a lower modulus of elasticity has a lower stiffness and a lower hardness than a material with a higher modulus of elasticity. As general guidelines, the modulus of elasticity of the material forming at least bracket engaging portions 122, 126 should be less than about $31 \times 10^6$ psi, for example less than about $5 \times 10^6$ psi. The Knoop microhardness (a measure of surface indentation) of at least portions 122, 126, which engage bracket 30, should be less than about 500, for example less than about 300. By comparison, a typical ceramic bracket will have a Knoop microhardness of at least about 1000, and more typically, about 2000 and have a modulus of elasticity in excess of $50 \times 10^6$ psi. Exemplary materials for the bracket engaging portions 122, 126 include resin-based composites, such as filled polycarbonate, and stainless steels, for example 300 series stainless steel. Other polymer-based materials include polysulfones, nylons, polyurethanes, and other thermoplastics or thermosets. Other soft metallic materials include titanium, aluminum, brass, zinc or alloys thereof. One skilled in the art may also appreciate that the material selected should be strong enough to withstand the gripping pressure applied to the bracket 30 without breaking.

In addition, at least a portion of one or both of the handles 112, 116 should be selected from a material having good resiliency so as to provide some flexing action when the handles 112, 116 are squeezed inward by the orthodontic practitioner. "Resilience" refers to the capacity of a material to exhibit considerable elastic recover on release of load. Alternatively, or in addition, at least a portion of one or both of the jaws may be made of a resilient material so as to provide the flexing action. The first and second plier portions 102, 106 may be made entirely from the same material, where the material is softer than the bracket material, or alternatively, one or both of the handles 112, 116 may be made of a different material than the jaws 114, 118 and/or bracket engaging portions 122, 126. The plier portions 102, 106 may be made by any suitable technique, including injection molding, die casting, or powder metallurgy processes.

Lever arm 130 may be made of any relatively rigid material, for example stainless steel. In an exemplary embodiment, the material for the lever arm 130 is harder and stiffer, i.e., less resilient, than the material of handles 112, 116 and/or the material of bracket engaging portions 122, 126. The lever arm may be made by any suitable technique, for example by stamping, metal injection molding, or die-casting.

The materials used for the tool 100 may be amenable to sanitizing for re-use, or the tool 100 may be disposable after a single-patient use.

Figure 6:
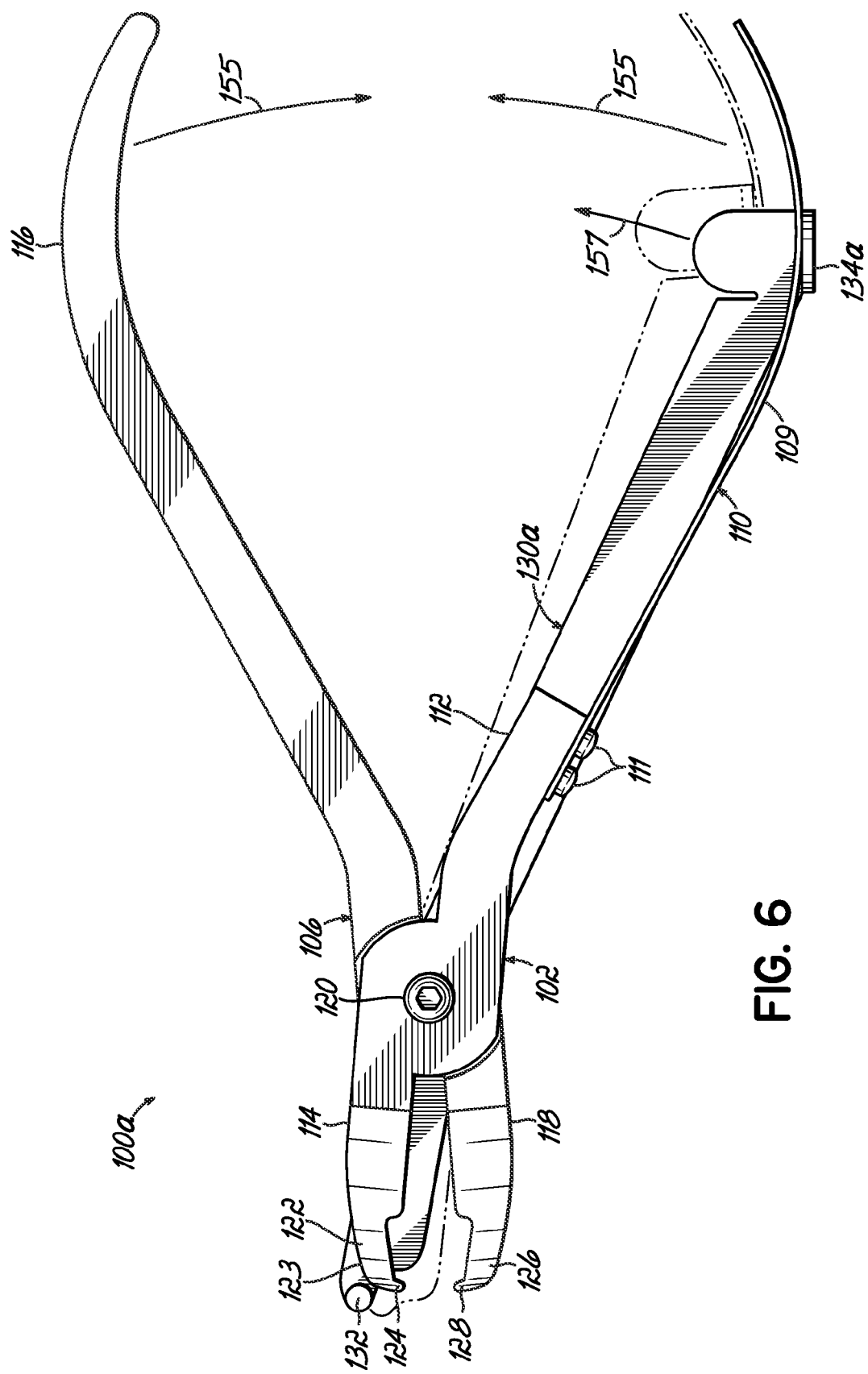
FIG. 6 illustrates a side elevation view of yet another exemplary embodiment of a debonding tool for removing an orthodontic bracket in accordance with the present invention.

An alternative embodiment of a tool of the present invention is illustrated in side elevation view in FIG. 6. In tool 100a, first plier portion 102 includes a resilient spring member 110 attached to handle 112, such as by one or a pair of rivets 111. Spring member 110 may be made, for example, from spring steel, a nickel-titanium alloy or other superelastic material, or other metallic material of high resilience. Spring member 110 provides the flexing action desirable at the handle end of the tool 100a. The remaining portions of the tool 100a can then be made of a stiffer material, provided that the bracket engaging portions 122, 126 are softer than the bracket material to minimize or avoid point loading of the bracket material. For example, the rest of tool 100a may be made of 300 series stainless steel. The lever arm may be made of the same materials contemplated for tool 100, for example stainless steel.

It will be appreciated that, as an alternative to forming at least part of one or both plier portions 102, 106 from a material that is more resilient than the material of lever arm 130, the resilience of first and second plier portions 102, 106 relative to lever arm 130 may be controlled by appropriate selection of the geometry of tool 100. Accordingly, in an exemplary embodiment, the geometry of at least one of the first and second plier portions 102, 106 is selected to provide more resilience than the geometry of the lever arm 130. In such an embodiment, the first and second plier portions 102, 106 and lever arm 130 may be formed from the same material, but the geometry of the components results in a difference of resiliency.

Also depicted in FIG. 6 is a variation regarding the opposing pin 134 of the lever arm 130. In the embodiment of tool 100 shown in FIGS. 1, 2A, 2B, 3 and 5, the pin 134 was positioned on the interior surface 113 of handle 112 such that when the handle 112 is squeezed inward, the lever arm 130 is urged inward. However, as shown in FIG. 6, a tab or protrusion 134a may be positioned adjacent an exterior surface 109 of spring member 110 (or handle 112 in other embodiments). In this case, the protrusion 134a is urged inward by the orthodontic practitioner, as indicated by arrow 157, and the protrusion 134a urges the spring member 110 inward, as indicated by arrow 155. Thus, the present invention includes embodiments in which a pin 134 or a protrusion 134a is positioned interiorly or exteriorly, or both, of the handle 112. In both embodiments, the tooth engaging member, such as pin 132, will be urged into contact with the tooth surface 32a to facilitate debonding of the bracket 30.

Figure 7:
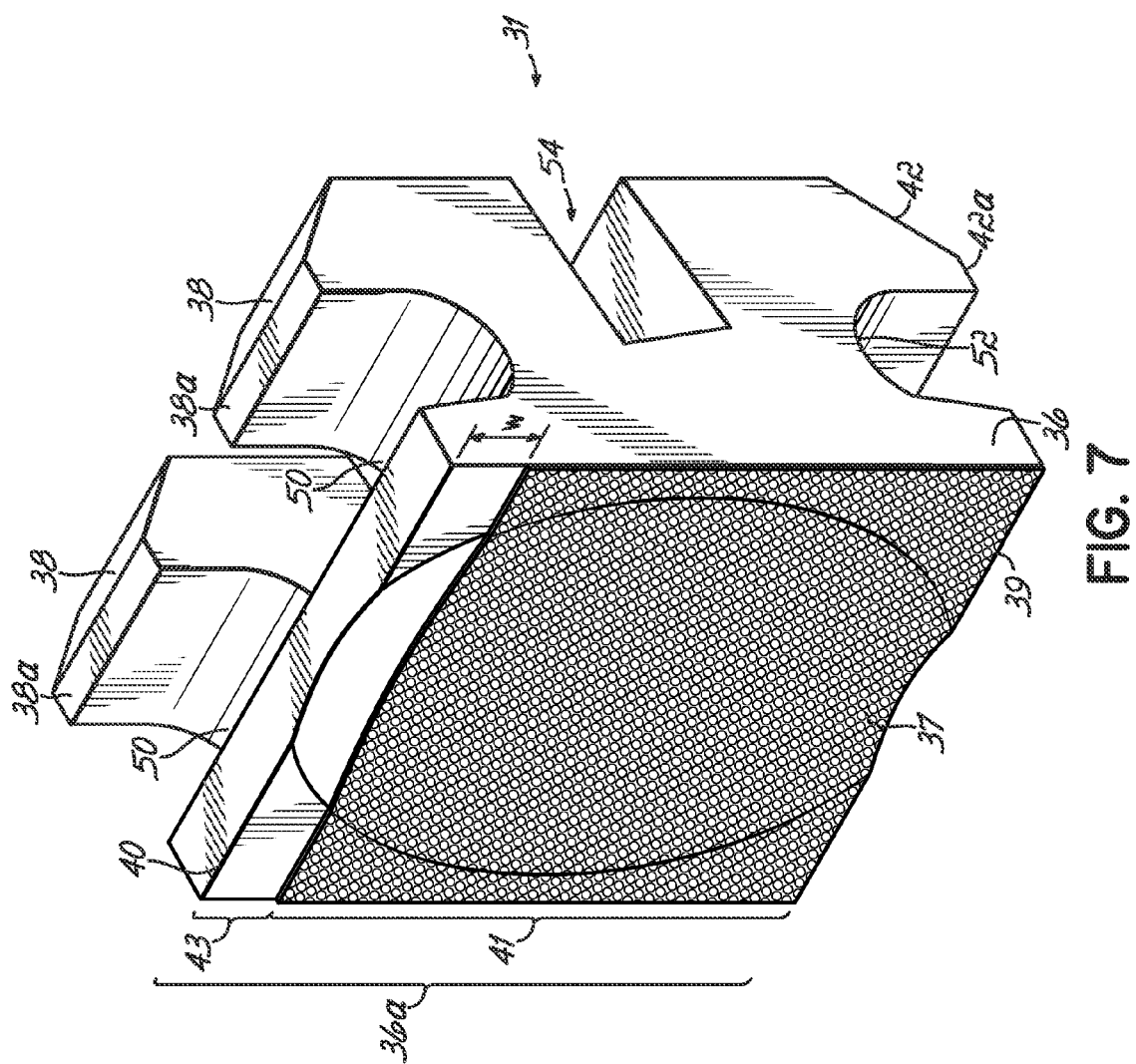
FIG. 7 is a perspective view of a bracket having a modified bonding base.
Figure 7A:
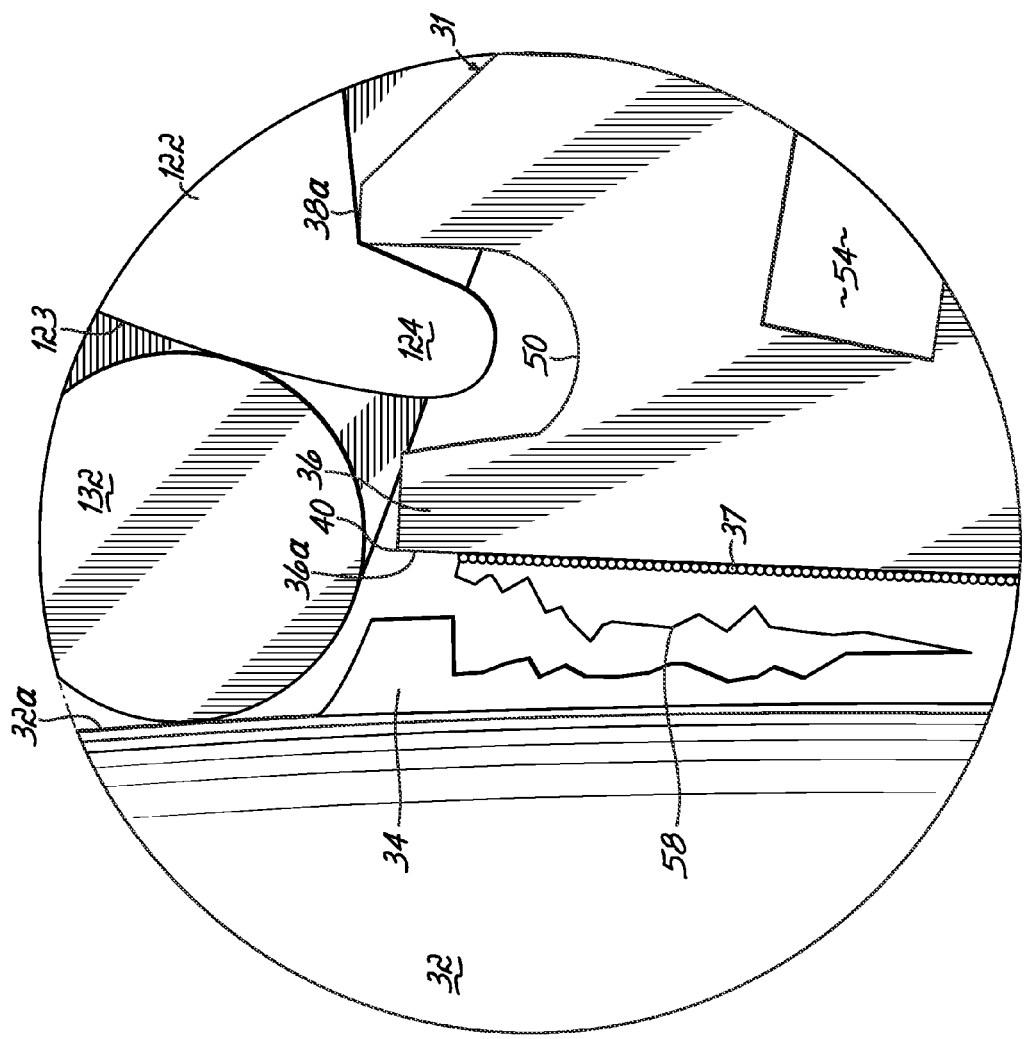
FIG. 7A is a fragmented, enlarged view similar to FIG. 5A detailing the breakage of the adhesive bond along the gingival side of the modified bracket of FIG. 7 during removal of the bracket from the tooth.

With reference to FIGS. 7 and 7A, a bracket 31 is depicted, which may be removed by the tool 100 and method of the present invention. In bracket 31, the bonding surface 36a has been modified from that of bracket 30, although this is not necessary for the present invention. Generally the bond interface between the adhesive layer 34 and bracket base 36 is referred to as a bonding pad, and may include various elements to facilitate mechanically bonding bracket 30, 31 to tooth surface 32a. For example, bonding structures for providing undercuts and/or increased bonding surface area are useful on surface 36a. In one embodiment of the invention, and as shown in FIGS. 7 and 7A, surface 36a includes bonding balls 37 which provide undercuts for mechanically bonding bracket 31 and tooth 32. The balls 37 are formed of conventional materials, as appreciated by those of ordinary skill in the art, and may have varying dimensions, such as having a diameter in the range from about 0.001 to about 0.005 inch. The present invention is not limited to mechanically bonding balls 37, as shown, and surface 36a may include other structures or projections thereon to provide the necessary surface area and/or undercuts for mechanically securing bracket 31 to tooth 32. For example, surface 36a may include a mesh comprising interwoven filaments of suitable material, such as metal, adhered to surface 36a by a suitable method, such as by diffusion bonding, sintering, soldering, or welding.

In the embodiment depicted in FIGS. 7 and 7A, bracket surface 36a is not completely or fully covered with the mechanically bonding balls 37 described above. Rather, bonding area 41 along a major portion of surface 36a, extending from an occlusal edge 39 and continuing in a gingival direction to a gingival edge 40 of surface 36a, is provided with balls 37. The remaining surface area 43 along the gingival edge 40, and extending inwards in the occlusal direction is free or void of balls 37. Area 43 is therefore not configured to provide a mechanical bond with adhesive layer 34 and, therefore, has less adhesion than the area covered with balls 37. As one alternative, area 43 may have a lower density of balls 37 (i.e., a lower number of balls per unit area) than the remainder of surface 36a. Adhesive layer 34 contacting area 43 will generally not form a chemical bond to surface 36a, particularly where surface 36a is formed of ceramic or metal materials. Thus, despite adhesive layer 34 contacting area 43, this portion of bracket base 36 does not form a significant bond with tooth surface 32a. In this fashion, area 43 provides gingival edge 40 with lower bond strength for ease of removing bracket 31 from tooth surface 32a, and particularly by the tool 100 and methods provided in the present invention. As shown in FIG. 7, the width "w" of area 43 is about 0.01 to about 0.03 inch. In one embodiment, area 43 has a width ranging from about 0.015 to about 0.025 inch. By reducing the mechanical fixation along the gingival edge 40 of bracket 31, a reduced debonding force, such as up to about 30% less than the debonding force used to remove prior art brackets in accordance with U.S. Pat. No. 6,382,965, is sufficient to debond or remove bracket 31 from tooth 32. Non-bonded area 43 allows the breaking or fracturing of the adhesive layer 34 with a force smaller than traditionally needed for removal of the bracket. In addition, elimination or reduction of a mechanical bond along gingival edge 40 does not significantly affect the bond strength and/or bond reliability during treatment.

In another embodiment of the invention, the entire surface area 36a of base of bracket 31, i.e., both areas 41 and 43, may be completely provided with balls 37 or other projecting structures for providing mechanically bonding undercuts on surface 36a. However, a portion of the balls 37 along the gingival edge 40, and defining a non-bonding area, similar to that of area 43, may be covered, coated, crushed or otherwise altered to reduce the mechanical bond with an adhesive layer 34. For example, a suitable coating (not shown) may be applied over a desired portion of the balls 37 on bracket base 36, extending in the occlusal direction from the gingival edge 40, for a distance in the range from about 0.015 to about 0.025 inch. Such a covering or coating, over balls 37, would prevent a mechanical bond between balls 37 and adhesive 34 along the gingival edge 40. This embodiment, therefore, reduces the force necessary for debonding or removing bracket 31 from a tooth surface 32a.

With reference to FIG. 7, bracket 31 further includes a pair of gingival tie wings 38 and a pair of occlusal tie wings 42. Thus, gingival tie wing 38 may be a single tie wing or a pair of tie wings, and similarly, occlusal tie wing 42 may be one or a pair. In this conventional configuration depicted in FIG. 7, recess 50 is provided between base 36 and the pair of gingival tie wings 38 and opposite recess 52 is provided between base 36 and the pair of occlusal tie wings 42.

In a method of the present invention for debonding a bracket from a tooth surface, a first surface and an opposite second surface of an orthodontic bracket bonded to a tooth are engaged with a plier-type tool. The plier-type tool includes first and second plier portions with opposing bracket engaging portions and opposing handles pivotally coupled to one another. A lever arm, which may be moveable independently of the first and second plier portions, is pivotally coupled to the plier portions and has a tooth engaging member at one end thereof. The handles of the tool are squeezed inwardly to grip the bracket thereby applying a compressive force by the opposing bracket engaging portions to the first and second surfaces and thereby moving the tooth engaging member into engagement with the tooth surface. The bracket is then pivoted about an axis lying in a plane generally parallel to a plane defined by the base to apply a tensile force to a first side of the bracket in a direction away from the tooth, the tensile force applied to the first side being substantially greater than any tensile force directed away from the tooth which may be applied to the side of the bracket located opposite to the first side, and fracturing the adhesive between the bracket and the tooth under the tensile force applied to the first side of the bracket to remove the bracket from the tooth.

Figure 8:
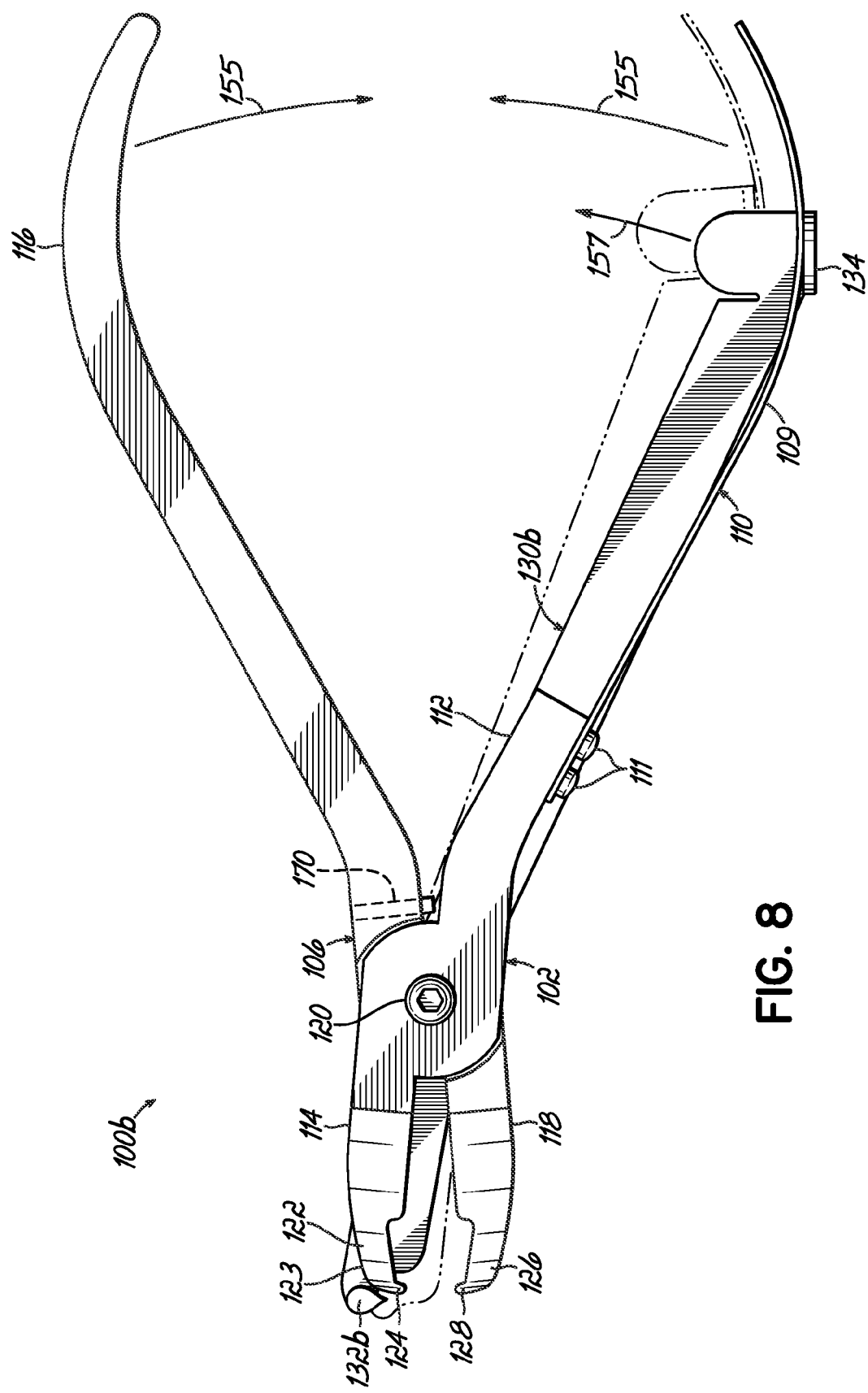
FIG. 8 is a side elevation view, similar to FIG. 6, illustrating another exemplary embodiment of a debonding tool for removing an orthodontic bracket.

While FIGS. 1-6 depict embodiments of a debonding tool wherein a tooth engaging member has been depicted as a pin 132, it will be appreciated that the tooth engaging member may comprise various other structure suitable for engaging the surface of a tooth to facilitate debonding an orthodontic bracket, as described above. As a non-limiting example, FIG. 8 depicts an embodiment of a debonding tool 100b wherein lever arm 130b includes a tooth engaging member in the form of a wedge-shaped boss 132b. Tool 100b further includes a stop member 170, depicted herein as an adjustable set screw threadably coupled to the second plier portion 106, for controlling the minimum gap between first and second jaws 114, 118 and their corresponding bracket engaging portions 122, 126 when first and second handles 112, 116 are squeezed together. While stop member 170 is shown and described as a set screw, it will be appreciated that various other structure suitable for controlling the minimum gap between bracket engaging portions 122, 126 may alternatively be used.

Figure 9:
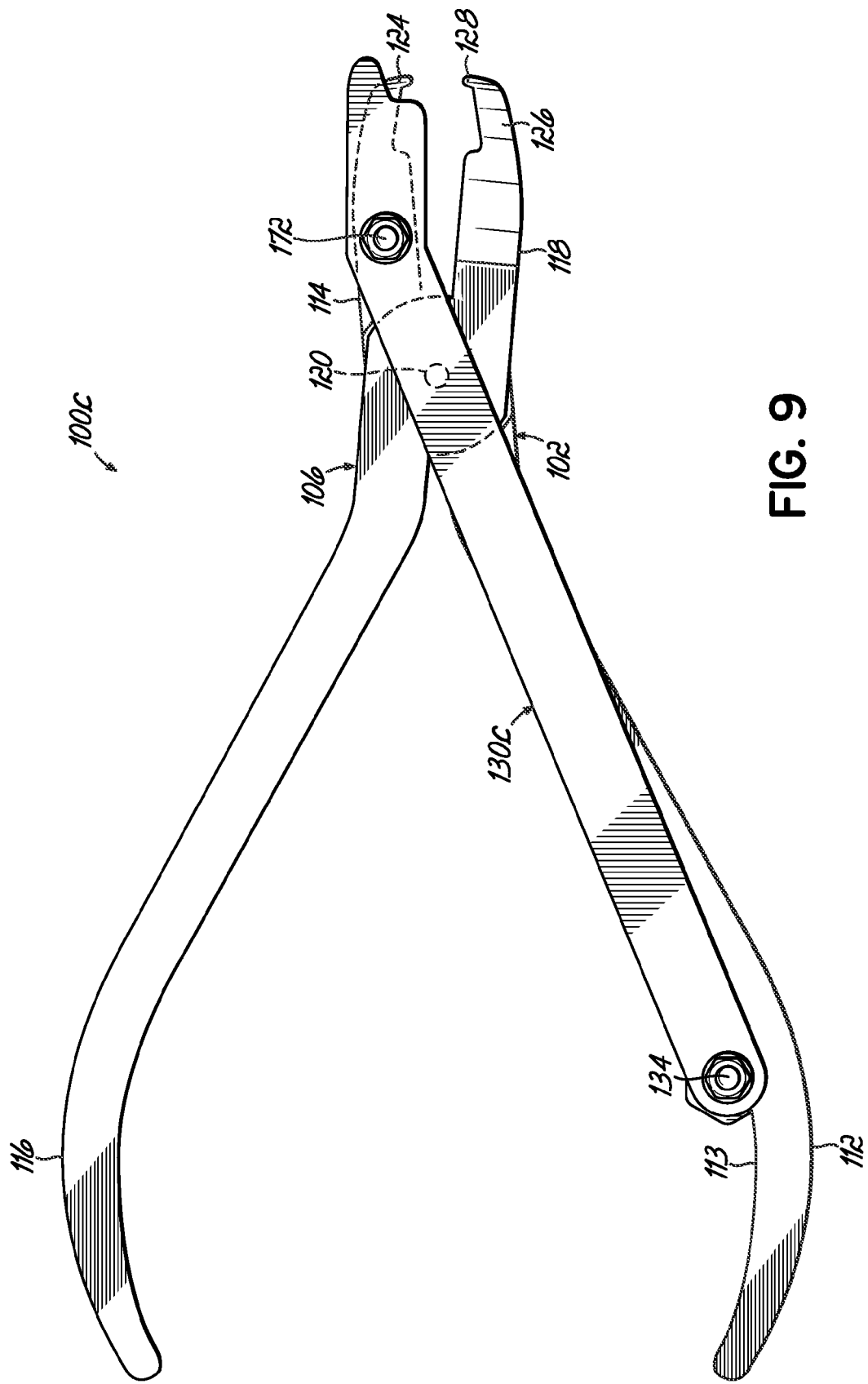
FIG. 9 is a side elevation view, similar to FIG. 2, illustrating yet another exemplary embodiment of a debonding tool for removing an orthodontic bracket.

FIG. 9 illustrates yet another exemplary debonding tool 100c similar to tools 100, 100a and 100b shown and described above, and like features have been similarly numbered. In this embodiment, however, lever arm 130c is pivotally coupled to the first jaw 114 at a pivot joint 172 that is separate from the pivot joint 120, which couples the first and second plier portions 102, 106. Accordingly, the center of rotation of lever arm 130c is different from the centers of rotation of the first and second plier portions 102, 106 and may be selected to provide a different amount of motion of the tooth engaging member (not shown) relative to the bracket engaging portions 122, 126.

According to one embodiment of the invention, the gripping forces applied to the orthodontic bracket 31 by the bracket engaging portions 122, 126 do not exceed approximately 40,000 psi to avoid damaging the bracket (e.g., breaking, crushing, or fracturing the bracket). In another embodiment, the gripping forces do no exceed approximately 20,000 psi.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A dental instrument for debonding an orthodontic bracket from a surface of a tooth, comprising:
   a first plier portion comprising a first handle and a first jaw for engaging an orthodontic bracket;
   a second plier portion comprising a second handle and a second jaw for engaging the orthodontic bracket;
   said first and second plier portions coupled for pivotal movement relative to one another; and
   a lever arm comprising a first end and a second end, said first end proximate said first jaw of said first plier portion, said first end including a tooth contacting member;
   said lever arm pivotally movable relative to at least one of said first plier portion or said second plier portion;
   said tooth contacting member positioned on said first end of said lever arm and extending across said first jaw and transverse to a plane defined by said first plier portion such that said tooth contacting member is moved between said first jaw and the tooth surface and in a direction toward said second jaw when said first jaw and said second jaw are engaged with the orthodontic bracket and said second end of said lever arm is pivotally manipulated in a direction toward said second handle;
   wherein at least a part of at least one of said first plier portion or said second plier portion has greater flexibility than said lever arm and said lever arm moves said tooth contacting member relative to said first jaw after said first jaw and said second jaw are engaged with the orthodontic bracket and said first handle, said second handle, and said lever arm are pivotally manipulated in directions toward one another.

2. The instrument of claim 1, wherein said first plier portion, said second plier portion, and said lever arm are pivotally movable about a common pivot center.

3. The instrument of claim 1, wherein said lever arm is movable independently of said first and second plier portions.

4. The instrument of claim 1, wherein said lever arm is operatively coupled to said first handle for movement with said first handle.

5. The instrument of claim 4, wherein said lever arm is configured to engage said first handle and thereby facilitate movement of said lever arm with said first handle.

6. The instrument of claim 1, wherein said first handle includes a spring member comprising a material having a lower modulus of elasticity than a material of said first jaw.

7. The instrument of claim 1, wherein said first jaw includes a first nib and said second jaw includes a second nib, said first and second nibs extending inwardly toward each other and adapted to engage the orthodontic bracket under respective gingival and occlusal tie wings.

8. The instrument of claim 1, wherein said tooth contacting member comprises a pin.

9. The instrument of claim 1, wherein said tooth contacting member is selectively adjustable on said first end to vary a position of said tooth contacting member relative to said first jaw.

10. The instrument of claim 1, wherein said tooth contacting member contacts said first jaw and the tooth surface when said tooth contacting member is moved between said first jaw and the tooth surface.

11. A dental instrument for debonding an orthodontic bracket from a surface of a tooth, comprising:
    a first plier portion comprising a first handle and a first jaw for engaging an orthodontic bracket;
    a second plier portion comprising a second handle and a second jaw for engaging the orthodontic bracket;
    said first and second plier portions coupled for pivotal movement relative to one another; and
    a lever arm comprising a first end proximate said first jaw of said first plier portion, said first end including a tooth contacting member;
    said lever arm pivotally movable relative to at least one of said first plier portion or said second plier portion;
    wherein at least a part of at least one of said first plier portion or said second plier portion has greater flexibility than said lever arm and said lever arm moves said tooth contacting member relative to said first jaw after said first jaw and said second jaw are engaged with the orthodontic bracket and said first handle, said second handle, and said lever arm are pivotally manipulated in directions toward one another.

12. The instrument of claim 11, wherein said greater flexibility is provided by a geometry of at least part of at least one of said first plier portion or said second plier portion.

13. The instrument of claim 11, wherein said greater flexibility is provided by a material forming at least part of at least one of said first plier portion or said second plier portion.

14. The instrument of claim 13, wherein said first and second plier portions comprise a resilient material having a modulus of elasticity less than $31 \times 10^6$ psi.

15. The instrument of claim 13, wherein at least one of said first handle or said second handle has greater flexibility than said lever arm.

16. The instrument of claim 13, wherein at least part of at least one of said first handle or said second handle has greater flexibility than said lever arm.

17. The instrument of claim 13, wherein at least a portion of said first handle comprises a resilient material having a modulus of elasticity less than $31 \times 10^6$ psi.

18. The instrument of claim 17, wherein said lever arm comprises a material having a higher modulus of elasticity than said resilient material of said portion of said first handle.

19. The instrument of claim 11, wherein at least one of said first jaw or said second jaw has greater flexibility than said lever arm.

20. The instrument of claim 18, wherein at least a portion of said first jaw comprises a resilient material having a modulus of elasticity less than $31 \times 10^6$ psi.

21. The instrument of claim 20, wherein said lever arm comprises a material having a higher modulus of elasticity than said resilient material of said portion of said first jaw.

22. The instrument of claim 11, wherein said at least part of at least one of said first plier portion or said second plier portion is sufficiently flexible such that gripping forces are applied to the orthodontic bracket by said first and second jaws without damaging the orthodontic bracket when said first handle, said second handle, and said lever arm are pivotally manipulated in directions toward one another.

23. The instrument of claim 22, wherein said gripping forces applied by said first and second jaws do not exceed approximately 40,000 psi.

* * * * *

UNITED STATES PATENT AND TRADEMARK OFFICE
CERTIFICATE OF CORRECTION

| | |
|---|---|
| PATENT NO. | : 7,581,949 B2 |
| APPLICATION NO. | : 11/563592 |
| DATED | : September 1, 2009 |
| INVENTOR(S) | : Farzin-Nia |

Page 1 of 1

It is certified that error appears in the above-identified patent and that said Letters Patent is hereby corrected as shown below:

Column 13
Line 1, CLAIM 20, reads "The instrument of claim 18, wherein at least" and should read -- The instrument of claim 19, wherein at least --.

Signed and Sealed this

Thirteenth Day of April, 2010

David J. Kappos
*Director of the United States Patent and Trademark Office*